(12) United States Patent  
Schumann

(10) Patent No.: US 6,174,421 B1  
(45) Date of Patent: Jan. 16, 2001

(54) SENSOR FOR DETERMINING THE CONCENTRATION OF OXIDIZABLE ELEMENTS IN A GAS COMPOUND

(75) Inventor: Bernd Schumann, Rutesheim (DE)

(73) Assignee: Robert Bosch GmbH, Stuttgart (DE)

(*) Notice: Under 35 U.S.C. 154(b), the term of this patent shall be extended for 0 days.

(21) Appl. No.: 09/202,313

(22) PCT Filed: Mar. 3, 1997

(86) PCT No.: PCT/DE97/00380

§ 371 Date: Mar. 22, 1999

§ 102(e) Date: Mar. 22, 1999

(87) PCT Pub. No.: WO97/47962

PCT Pub. Date: Dec. 18, 1997

(30) Foreign Application Priority Data

Jun. 11, 1996 (DE) ............................................. 196 23 212

(51) Int. Cl.[7] ................................................. G01N 27/407
(52) U.S. Cl. ...................... 204/424; 204/426; 204/291
(58) Field of Search .................... 204/424, 426, 204/427, 428, 429, 425, 291; 205/783.5, 784, 784.5, 785, 781; 429/33

(56) References Cited

U.S. PATENT DOCUMENTS

| | | | |
|---|---|---|---|
| 5,520,789 | * | 5/1996 | Takahashi et al. .................... 204/424 |
| 5,630,920 | * | 5/1997 | Friese et al. .......................... 204/424 |
| 5,814,719 | * | 9/1998 | Suzuki et al. ........................ 73/23.31 |
| 6,022,464 | * | 2/2000 | Schumann ............................ 204/424 |

* cited by examiner

Primary Examiner—Robert J. Warden, Sr.  
Assistant Examiner—Kaj K. Olsen  
(74) Attorney, Agent, or Firm—Kenyon & Kenyon

(57) ABSTRACT

Sensor for measuring the concentration of oxidizable constituents in a gas mixture, in particular for measuring one or more $NO_x$, $CO$, $H_2$ gases, and preferably unsaturated hydrocarbons, by measuring the voltage between a measuring electrode a reference electrode or by measuring the voltage between two measuring electrodes. A porous solid electrolyte makes it possible to dispense with a reference gas atmosphere, thus providing greater miniaturization and simplifying the design. The selectivity toward individual measuring gas constituents can be improved by selecting the measuring electrode materials, in particular by using semiconductors.

21 Claims, 1 Drawing Sheet

SENSOR FOR DETERMINING THE CONCENTRATION OF OXIDIZABLE ELEMENTS IN A GAS COMPOUND

FIELD OF THE INVENTION

The present invention relates to a sensor for measuring the concentration of oxidizable constituents in a gas mixture, in particular for measuring one or more of the gases $NO_x$, CO, $H_2$, and preferably unsaturated hydrocarbons.

BACKGROUND INFORMATION

Elevated concentrations of oxidizable constituents, in particular, of $NO_x$, CO, $H_2$, and hydrocarbons, can occur in the exhaust gases of spark-ignition and diesel engines, internal-combustion machines and incineration plants, e.g. as the result of a component malfunction such as an injection valve or as the result of incomplete combustion. To optimize the combustion reaction, it is therefore necessary to determine the concentration of these exhaust gas constituents. A method for measuring oxidizable gases is described in Unexamined Japanese Patent Application No. 60-61654, in which a stoichiometric reaction with oxygen takes place at a first measuring electrode made of platinum-class metals, and quasi-equilibrium states are established at one or more additional metallic measuring electrodes with reduced catalytic activity for the oxygen equilibrium reaction. Nernst voltages E1 and E2 are measured between the measuring electrodes and a reference electrode, which is exposed to a reference gas having a constant oxygen partial pressure, and the concentrations of the gas constituents calculated from the difference between these voltages on the basis of calibration curves.

SUMMARY OF THE INVENTION

A sensor according to the present invention provides greater miniaturization, a simplified design, and more cost-effective production than a conventional sensor. This is achieved according to the present invention by the fact that the solid electrolyte is porously sintered. The molecules of the measuring gas can thus diffuse through the solid-electrolyte pores and reach the reference electrode, where thermodynamic equilibrium is established. This exposes the reference electrode to an oxygen partial pressure which corresponds to the thermodynamic equilibrium. It is therefore not necessary to supply a reference gas, which greatly simplifies the sensor layout.

The thermodynamic equilibrium can also be advantageously established even in the solid electrolyte by selecting a catalytically active solid electrolyte material. A particular advantage of this is that it enables the gases interfering with the reference signal to be selectively oxidized, simplifying signal analysis or even making it possible in the first place. Not only the solid electrolytes but also the measuring electrodes can be suitably porous, which further improves the diffusion of the measuring gas molecules to the reference electrode.

Mixing additives made of the same substances as the electrodes into at least one layer of the solid electrolyte which lie adjacent to the electrodes improves electrode adhesion and thus also the service life of the sensor. It is also especially advantageous to construct the measuring electrodes from semiconductors, which can significantly increase selectivity toward the individual gas constituents to be detected.

DETAILED DESCRIPTION

Figure 1:
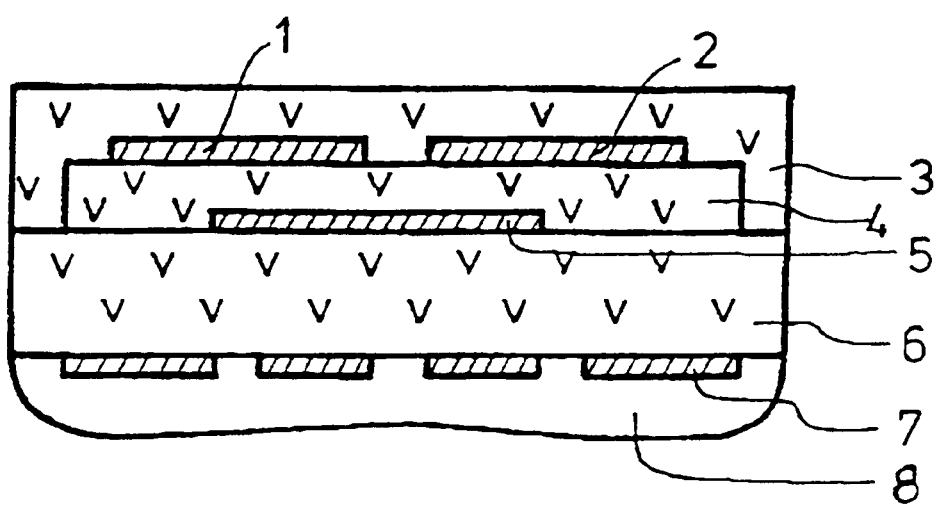
FIG. 1 shows a cross-section of a sensor according to the present invention.

FIG. 1 shows a cross-section of a sensor according to the present invention. One large surface of an insulating flat ceramic substrate 6 contains, in vertically arranged layers, a reference electrode 5, preferably made of platinum, a porous solid electrolyte 4, measuring electrodes 1 and 2, and a gas-permeable protective layer 3. A heating device 7 with a cover 8 is mounted in the opposite large surface.

To measure the concentration of oxidizable constituents in exhaust gases, the sensor is heated to a temperature between 300 and 1,000° C., advantageously to 600° C., using heating device 7.

The measuring gas diffuses through the porous solid electrolyte to reference electrode 5, which catalyzes the establishment of the oxygen equilibrium potential. Measuring electrodes 1, 2 are designed to have reduced catalytic activity in the oxygen equilibrium reaction. On at least one measuring electrode, the sensor generates a cell voltage via the oxygen ion conducting solid electrolyte by a first half-cell reaction initiated with the help of the reference electrode and a second half-cell reaction influenced by the oxidizable gas constituents to be measured. The concentrations of the gas constituents is determined from the voltage values on the basis of the calibration curves.

In its simplest form, the sensor according to the present invention can be used with one reference electrode which catalyzes the establishment of gas mixture equilibrium and with one measuring electrode which cannot or can only slightly catalyze the establishment of gas mixture equilibrium. However, it is also possible to install two measuring electrodes, as shown in FIG. 1, or even multiple electrodes, each with different catalytic activity for establishing oxygen equilibrium states. The measuring electrodes then respond with different voltages in relation to the reference electrode, depending on the type of gas.

In arrangements with two or more measuring electrodes with different catalytic activities, it is also possible to evaluate voltages between the measuring electrodes in order to measure oxidizable gases. Measuring voltages between electrodes that are on the same plane and positioned equidistant from the heating device, such as electrodes 1 and 2 in FIG. 1, also disables the Seebeck effect.

In arrangements with at least two measuring electrodes, it is also possible to completely or at least partially compensate for cross-sensitivity of a first measuring electrode us using the signal of an additional measuring electrode by adjusting the sensitivity of this additional measuring electrode to the interfering gas constituents.

According to an additional embodiment, the solid electrolyte is designed in such a way, e.g. by mixing in 0.01% to 10% by volume of platinum powder into at least one layer of the solid electrolyte facing the reference electrode, that the solid electrolyte catalytically converts the gases to be measured so that only the gases corresponding to the thermodynamic equilibrium reach the reference electrode, or that the solid electrolyte converts only the gases interfering with the reference signal.

According to an additional embodiment, one or more measuring electrodes, in addition to the solid electrolyte, are porous, thereby facilitating the diffusion of gas to the reference electrode.

Concerning the measuring electrode composition, it is possible to select metal electrode substances like those described, for example, in Unexamined Japanese Patent Application No. 60-61654, or semiconductors with a high specific sensitivity toward certain oxidizable gases. Especially suitable are semiconducting oxides or mixed oxides, which can be doped with an acceptor and/or donor having a concentration, for example, of between 0.01% and 25%. The acceptor is incorporated into the semiconductor as, for example, a solid solution or a segregated constituent. The high sensitivity, e.g. of acceptor- and donor-doped n-type titanium oxide, in particular to unsaturated hydrocarbons, is due to the adsorbent interaction between the orbitals of the pi bonds of the unsaturated hydrocarbons and the acceptor sites on the semiconductor surface.

To prevent the conductivity-reducing acceptor component from becoming fully electronically active, it is advantageous to add to the electrode a conductivity-increasing donor, in particular in a higher concentration than the acceptor.

The following example describes a method for producing a sensor according to the present invention: rutile doped with 0.5% to 15%, for example 7%, niobium and 0.25% to 7%, for example 3%, of one of transition metals nickel, copper or iron is screen-printed in a 30 $\mu$m layer onto a substrate on which are mounted a reference electrode, preferably made of platinum, and, on top if this, a solid electrolyte layer. A heating device is attached to the opposite side of the substrate. The sensor is sintered for 90 minutes at 1,200° C. with a heating/cooling ramp of 300° C./hour. After sintering, the solid electrolyte has pores ranging in size from 10 nm to 100 $\mu$m.

An attached platinum conductor path, which is insulated from the solid electrolyte and contacts only the measuring electrode, is used to measure the voltage between the reference and rutile electrodes at the cell formed in this manner with a resistance of 1 MOhm. In doing this, the sensor is heated by its heating device to a temperature of 600° C. A simulated exhaust gas containing 10% oxygen, 5% water, and 5% carbon dioxide, as well as 30 ppm sulfur dioxide, is used as the measuring gas. Oxidizable gases are then added in the quantities shown in the table.

For comparison, the last line in the following table shows the voltage values for a mixed-potential electrode made of 20% gold and 80% platinum, representing a measuring electrode according to the related art.

TABLE

Voltage values (in mV) as a function of the concentration of oxidizable gases and the composition of the measuring electrode

| Rutile electrode with 7% Nb and 3% oxidizable gases | Voltages in mV | | | Reference electrode, 20% |
|---|---|---|---|---|
| (ppm) | Ni | Cu | Fe | Au and 80% Pt |
| Propene 460 | 150 | 45 | 60 | 320 |
| 180 | 120 | 36 | 47 | 280 |
| 90 | 90 | 27 | 35 | 180 |
| H2  460 | 30 | 12 | 20 | 500 |
| 180 | 17 | 6 | 10 | 450 |
| 90 | 5 | 3 | 4 | 380 |
| CO  460 | 40 | 3 | 16 | 70 |
| 180 | 15 | — | 7 | 35 |
| 90 | 7 | — | 6 | 23 |

The table shows that a rutile semiconductor electrode with 7% niobium as the donor and 3% nickel as the acceptor demonstrates the greatest sensitivity to propene as the conductive substance. The gold-platinum system known from the related art, on the other hand, shows especially high cross-sensitivity to hydrogen.

What is claimed is:

1. A sensor for measuring a concentration of at least one oxidizable constituent in a gas mixture, comprising:
   a reference electrode catalyzing an establishment of a thermal equilibrium of the gas mixture;
   an ion-conducting solid electrolyte having at least one pore, the solid electrolyte including additives which catalyze oxidation of one of:
      the at least one oxidizable constituent, and
      the at least one oxidizable constituent that interferes with a reference gas in the gas mixture;
   at least one measuring electrode exposed to the at least one oxidizable constituent, the at least one measuring electrode being substantially unable to catalyze the establishment of the thermal equilibrium of the gas mixture; and
   a flat electrically insulating substrate,
   wherein the reference electrode, the solid electrolyte and the at least one measuring electrode are situated in vertical layers on a large surface of the substrate.

2. The sensor according to claim 1, wherein:
   the at least one oxidizable constituent includes at least one of $NO_x$, CO, $H_2$ gas and unsaturated hydrocarbons.

3. The sensor according to claim 1, wherein a size of the at least one pore is between 10 nm and 100 $\mu$m.

4. The sensor according to claim 1, wherein:
   the at least one measuring electrode has at least one pore.

5. The sensor according to claim 4, further comprising:
   at least two measuring electrodes.

6. The sensor according to claim 4, wherein:
   the reference electrode is composed of a first material;
   the at least one measuring electrode is composed of a second material; and
   the solid electrolyte includes at least two vertically arranged layers, a first layer of the at least two layers facing the reference electrode and composed of a third material which includes the first material, a second layer of the at least two layers facing the at least one measuring electrode and composed of a fourth material which includes the second material, the first layer being different from the second layer.

7. The sensor according to claim 1, wherein the at least one measuring electrode includes at least one semiconductor.

8. The sensor according to claim 7, wherein the at least one semiconductor is doped with at least one of an acceptor and a donor.

9. The sensor according to claim 8, wherein a first concentration of the donor is higher than a second concentration of the acceptor.

10. The sensor according to claim 8, wherein the donor is composed of a first element having a first valence, the at least one semiconductor being composed of a second element having a second valence, the first valence being higher than the second valence.

11. The sensor according to claim 10, wherein the donor is composed of at least one of tantalum and niobium.

12. The sensor according to claim 8, wherein:
   the at least one semiconductor is doped with the acceptor, the acceptor including at least one transition element.

13. The sensor according to claim 12, wherein the at least one transition element is at least one of nickel, copper, cobalt and chromium.

14. The sensor according to claim 13, wherein the at least one transition element is at least one of nickel, copper, cobalt and rare earths.

15. The sensor according to claim 12, wherein:
the acceptor is incorporated into the at least one semiconductor as one of a solid solution and a segregated constituent.

16. The sensor according to claim 8, wherein a concentration of at least one of the acceptor and the donor is between 0.01% and 25%.

17. The sensor according claim 16, wherein the at least one semiconductor is composed of 0.5% to 15% niobium and 0.25% to 7% nickel.

18. The sensor according claim 16, wherein the at least one semiconductor is composed of 7% niobium and 3% nickel.

19. The sensor according claim 7, wherein the at least one semiconductor is composed of one of an oxide, a single-phase mixed oxide and multi-phase mixed oxide.

20. The sensor according claim 19, wherein the at least one semiconductor is composed of one of a rutile oxide, a dirutile oxide and a further oxide, the further oxide including a mixture of the rutile oxide and the dirutile oxide.

21. The sensor according to claim 19, wherein the at least one semiconductor is composed of a titanium oxide.

* * * * *